United States Patent
Hegde et al.

(10) Patent No.: US 10,832,805 B2
(45) Date of Patent: Nov. 10, 2020

(54) METHOD AND SYSTEM FOR GENERATING ELECTRONIC MEDICAL REPORTS

(71) Applicant: Siemens Healthcare GmbH, Erlangen (DE)

(72) Inventors: Ananda Hegde, Bangalore (IN); Pavan Kumar, Bangalore (IN)

(73) Assignee: Siemens Healthcare GmbH, Erlangen (DE)

( * ) Notice: Subject to any disclaimer, the term of this patent is extended or adjusted under 35 U.S.C. 154(b) by 527 days.

(21) Appl. No.: 14/926,474

(22) Filed: Oct. 29, 2015

(65) Prior Publication Data
US 2017/0124290 A1 May 4, 2017

(51) Int. Cl.
*G16H 15/00* (2018.01)
*G16H 30/20* (2018.01)
*G06F 16/2457* (2019.01)
*G06F 16/2455* (2019.01)

(52) U.S. Cl.
CPC ............ *G16H 15/00* (2018.01); *G16H 30/20* (2018.01); *G06F 16/2455* (2019.01); *G06F 16/24578* (2019.01)

(58) Field of Classification Search
CPC ...... G06F 19/321; G06Q 50/22; G06Q 50/24; G16H 10/60; G16H 15/00; G16H 30/40
See application file for complete search history.

(56) References Cited

U.S. PATENT DOCUMENTS

| | | | |
|---|---|---|---|
| 5,986,662 A * | 11/1999 | Argiro | G06T 11/00 345/419 |
| 2004/0125131 A1 | 7/2004 | Phelps | |
| 2005/0267348 A1 * | 12/2005 | Wollenweber | A61B 6/032 600/407 |
| 2008/0119717 A1 * | 5/2008 | Profio | G16H 40/20 600/407 |
| 2009/0274384 A1 | 11/2009 | Jakobovits | |
| 2010/0332256 A1 * | 12/2010 | Schwartz | G06F 19/321 705/3 |

(Continued)

OTHER PUBLICATIONS

Mendelson, David S., and Daniel L. Rubin. "Imaging informatics: essential tools for the delivery of imaging services." Academic radiology 20.10 (2013): 1195-1212.

*Primary Examiner* — Jonathan Durant
(74) *Attorney, Agent, or Firm* — Lempia Summerfield Katz LLC (57) ABSTRACT

A search query for a predefined protocol name for the electronic medical report is generated. The search query is processed for the predefined protocol names. One or more predefined protocol names are identified from a plurality of protocol names in a protocol names database. An electronic medical report is generated using the one or more predefined protocol names. A rank for the protocol names is computed based on best matching criteria. The one or more of the identified predefined protocol names are selected based on the rank associated with the protocol name. The predefined protocol name is assigned to an appropriate field in an electronic medical report. A medical report database storing all the medical reports is indexed based on the predefined protocols so that the medical reports may be searched by querying the predefined protocol name.

13 Claims, 4 Drawing Sheets

(56) References Cited

U.S. PATENT DOCUMENTS

| | | | |
|---|---|---|---|
| 2011/0270843 A1* | 11/2011 | Albin | G06F 17/30864 707/741 |
| 2012/0035963 A1* | 2/2012 | Qian | G06Q 50/24 705/3 |
| 2012/0066197 A1* | 3/2012 | Rana | G06F 19/322 707/706 |
| 2013/0268852 A1 | 10/2013 | Hewett et al. | |
| 2013/0311472 A1* | 11/2013 | Cohen-Solal | G06F 19/321 707/737 |
| 2014/0094699 A1* | 4/2014 | Spillane | G16H 15/00 600/437 |
| 2014/0324477 A1* | 10/2014 | Oez | G06Q 10/10 705/3 |
| 2014/0379718 A1* | 12/2014 | Halter | G06F 19/321 707/738 |
| 2015/0081315 A1* | 3/2015 | Baker | G06Q 50/22 705/2 |

\* cited by examiner

METHOD AND SYSTEM FOR GENERATING ELECTRONIC MEDICAL REPORTS

BACKGROUND

The present embodiments relate to a method and system for generating electronic medical report. The method and system of the present embodiments may be used for generating electronic medical reports having uniform nomenclature in certain fields.

Currently in the healthcare environment, the diagnostic imaging field is heading towards standardization. When a patient is scheduled for an imaging examination, an imaging report is generated after the imaging examination is executed. The imaging exam may be conducted using various modalities such as X-ray, computerized tomography, magnetic resonance imaging and the like. Typically, when a patient is scheduled for an exam, the technicians provide the basic information such as, patient name, date of birth, scan type, and protocol used, required by the medical imaging modalities. Once the scanning is completed, all the data entered by the technician is recorded in Radiation Dosage Structured Report (RDSR) or images. The dosage information may be recorded in the RDSR by the imaging modality or the technician. Protocol name is one of the important fields in the RDSR, as the protocol name is useful at the time of auditing. Protocol name may be based on parameters such as body region, modality type, laterality, anatomic focus and the like. Generally, the technicians enter informal names as protocol names, which do not relate to any of the aforementioned parameters. In some cases, the protocol names may not include the required information such as body regions or anatomical region. Further, such informal naming practices lead to non-standardized naming practices across healthcare institutions. As a result, it is difficult to establish national registry, such as a radiation dosage national registry, to facilitate comparisons among different types of procedures using different medical imaging modalities across various healthcare institutions.

There are efforts to bridge this inconsistency by introducing uniformity in protocol names that are furnished in the RDSR. Organizations such as Radiological Society of North America (RSNA) are taking active steps in this direction. One of the initiatives RSNA has taken in this regard is the introduction of RadLex Playbook. RadLex Playbook aims to provide a standard system for naming radiology procedures based on the characteristics of a medical imaging exam such as modality or body part. The RadLex Playbook provides a unique RPID for each procedure. The RPIDs are to be entered in the RDSRs for making the naming convention standardized. The use of RPID also results in formation of national dosage registry where the dosage values of various procedures may be compared and improved.

At present, the task of finding out the RPID by a technician during/before the medical imaging procedure is not performed. The RPIDs are mapped to the informal names provided in the RDSRs during auditing. This is a cumbersome and time consuming task.

SUMMARY AND DESCRIPTION

The scope of the present invention is defined solely by the appended claims and is not affected to any degree by the statements within this summary.

There is need for an easier way to include standardized protocol names in the RDSR. The present embodiments may obviate one or more of the drawbacks or limitations in the related art. For example, medical reports that include predefined protocol names are generated. Including predefined protocol names in the medical reports is very beneficial during auditing, as the medical reports will have a standard terminology across healthcare institutions.

A method, a computing device, and a system for generating medical reports that include predefined protocol names are provided. The method and apparatus enables a technician to furnish the relevant predefined protocol names in a medical report before commencing the exam on a patient. The method includes, at act 62, generating a search query for a predefined protocol name for the electronic medical report. In an embodiment, the search query is generated by a user before commencing the imaging examination on the patient. In another embodiment, a computing device determines at least one characteristic of the medical image and automatically generates a search query based on the at least one characteristic of the medical image. For example, the computing device may determine characteristics of a medical image such as body region, modality type, and exam type from an appointment schedule. Based on this information, the computing device may generate a search query for a predefined protocol name based on the characteristics of the medical image. The search query for the predefined protocol names is processed. The search query is processed by extracting keywords that indicate a characteristic of a medical image. Thereafter, one or more analogous terms corresponding to the keywords are determined using a medical dictionary database. Further, a search phrase is generated based on the one or more analogous terms.

One or more predefined protocol names are identified from a plurality of protocol names in a protocol names database. The predefined protocol names are identified by comparing the analogous terms in the search phrase with one or more medical dictionary terms in the protocol names database. For the purpose of selecting the predefined protocol names, the protocol names database is indexed based on the medical dictionary terms that are present the medical dictionary database 38. Thereafter, one or more predefined protocol names corresponding to the matching terms are retrieved from the protocol names database.

A rank for the protocol names is computed based on best matching criteria. For example, the best matching criteria may be a relevance of the search phrase with the medical dictionary terms and the number of terms in the search phrase matching with indexed medical dictionary terms.

Thereafter, one or more of the identified predefined protocol names are selected based on the rank associated with the protocol name. The predefined protocol names may be selected manually by the technician operating the imaging modality. An electronic medical report is generated using the one or more predefined protocol names.

BRIEF DESCRIPTION OF THE DRAWINGS

The above mentioned and other features will now be addressed with reference to the accompanying drawings. The illustrated embodiments are intended to illustrate but not limit the invention.

DETAILED DESCRIPTION

Various embodiments are described with reference to the drawings, where like reference numerals are used to refer like elements throughout. In the following description, for the purpose of explanation, numerous specific details are set forth in order to provide thorough understanding of one or more embodiments. Such embodiments may be practiced without these specific details.

Figure 1:
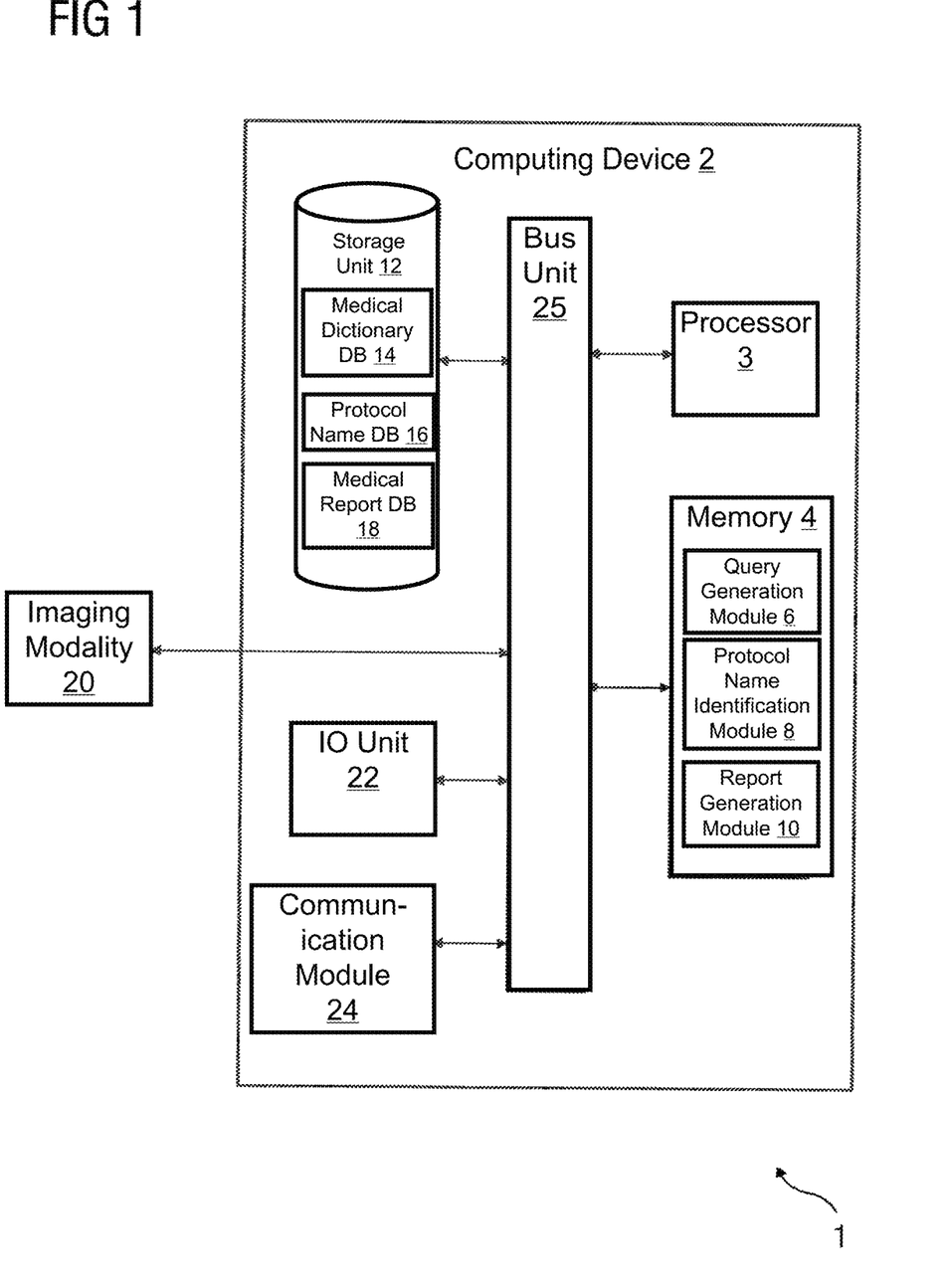
FIG. 1 illustrates an exemplary block diagram 1 of a computing device for generating electronic medical records, in accordance with an embodiment.

FIG. 1 illustrates an exemplary block diagram 1 of a computing device 2 for generating electronic medical records, in accordance with an embodiment. The computing device 2 includes a processor 3, a memory 4, a storage unit 12, an input/output (I/O) unit 22, and a communication module 24. The computing device 2 is also communicatively coupled to an imaging modality 20. The imaging modality 20 may include, but is not limited to, an X-ray modality, a magnetic resonance imaging (MRI) modality, a positron emission tomography (PET) modality, an ultrasound imaging modality and a computerized tomography (CT) modality. The aforementioned components are connected to each other by a bus unit 25. The processor 3, as used herein, may be any type of computational circuit, such as, but not limited to, a microprocessor, a microcontroller, a complex instruction set computing microprocessor, a reduced instruction set computing microprocessor, a very long instruction word microprocessor, an explicitly parallel instruction computing microprocessor, a graphics processor, a digital signal processor, or any other type of processing circuit. The processor 3 may also include embedded controllers, such as generic or programmable logic devices or arrays, application specific integrated circuits, single-chip computers, and the like.

The memory 4 may be volatile memory and non-volatile memory. A variety of computer-readable storage media may be stored in and accessed from the memory 4. The memory 4 may include any suitable elements for storing data and machine-readable instructions, such as read only memory, random access memory, erasable programmable read only memory, electrically erasable programmable read only memory, hard drive, removable media drive for handling compact disks, digital video disks, diskettes, magnetic tape cartridges, memory cards, and the like. As depicted, the memory 4 includes one or more modules for generating medical reports with predefined protocol names, according to one or more embodiments described above. The memory 4 includes a search query generation module 6, a protocol name identification module 8, and a report generation module 10. The search query generation module 6 includes processor executable instruction for generating a search query for the predefined protocol names. The search query generation module 6 is configured for generating a search query for a predefined protocol name for the electronic medical report. The search query generation module 6 is configured for determining at least one characteristic of the medical image. The characteristic of the medical image may include a body region, an exam type, and a modality type. Thereafter, the search query generation module 6 is configured for automatically generating a search query based on the at least one characteristic of the medical image. The protocol name identification module 8 is configured for processing the search query for the predefined protocol names. Further, the protocol name identification module 8 is configured for identifying one or more predefined protocol names from a plurality of protocol names in a protocol names database. The protocol name identification module 8 is configured for computing a rank for the protocol names based on best matching criteria. The best matching criteria is based on the terms in the search query and the analogous terms thereof. The protocol name identification module 8 is further configured for selecting the one or more of the identified predefined protocol names based on the rank associated with the protocol name. The report generation module 10 is configured for generating an electronic medical report using the one or more predefined protocol names. The report generation module 10 is further configured for assigning the uniform protocol name to an appropriate field in the electronic medical report.

The storage unit 12 may be a non-transitory storage medium configured for storing information such as medical dictionary, medical reports data, and protocol names data. In an exemplary embodiment, the storage unit 12 includes a medical dictionary database 14, a protocol names database 16, and a medical reports database 18. For example, the storage unit 12 includes a medical dictionary database that is referred to for generating a search phrase based on the search query. The storage unit 12 may be located at a remote location and may be accessed via a network connection. In one or more of the present embodiments, the information in the storage unit 12 may be utilized for searching an appropriate predefined protocol name for a medical report.

The input output module 22 may include a keyboard, keypad, touch sensitive display screen, mouse, and the like. The input/output devices 22 enable the user to interact with the device 3 for controlling the operating state. For example, a display unit may display a screen that includes one or more graphical objects indicating the status associated with the processing of speech signals.

The device 2 further includes a communication module 24 for communicating with other devices via a network connection. The communication module 24 may include a Wi-Fi transceiver, a network interface card (NIC), and the like.

Figure 2:
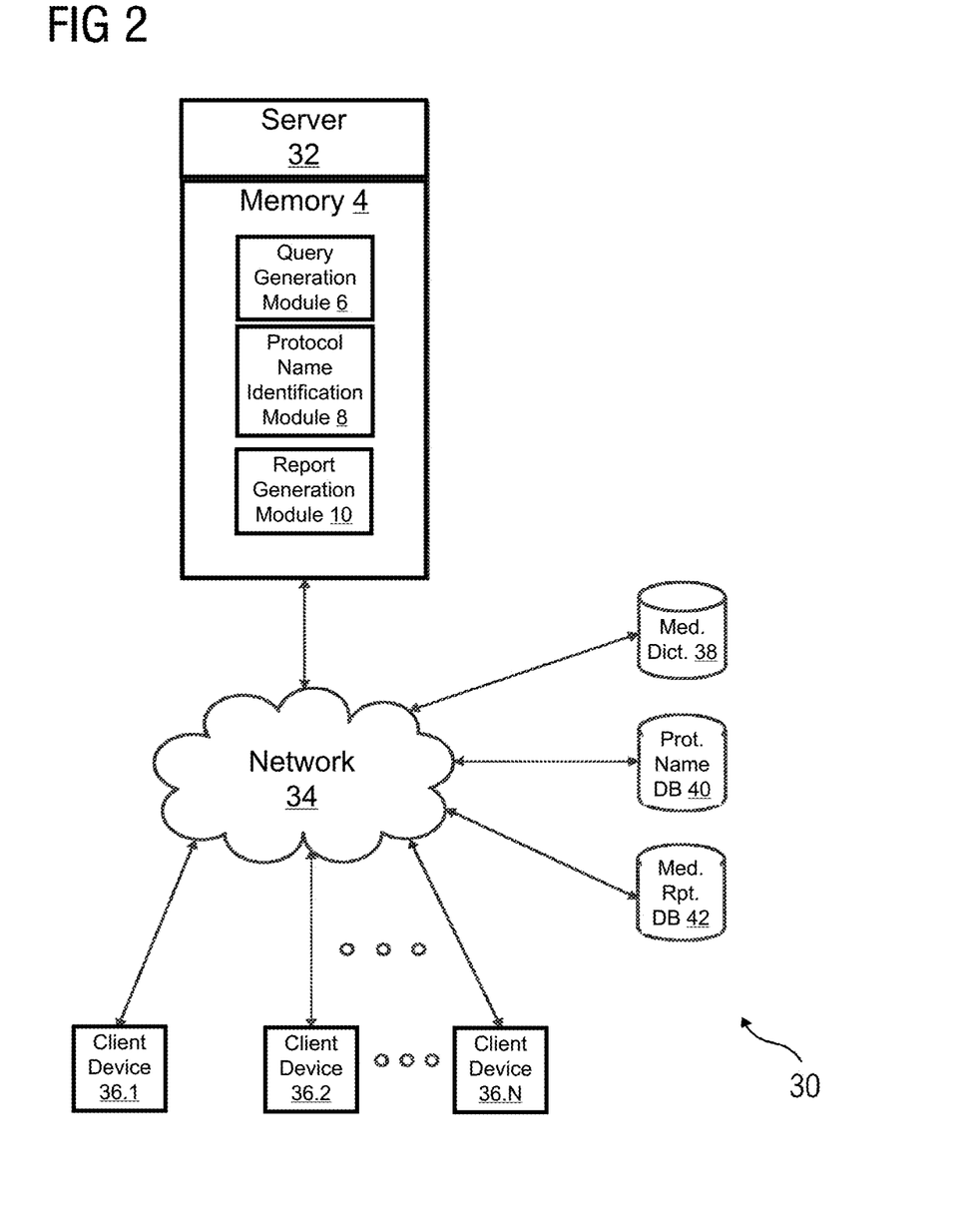
FIG. 2 illustrates an exemplary block diagram of a system for generating medical reports, in accordance with an embodiment.

FIG. 2 illustrates an exemplary block diagram of a system 30 for generating medical reports, in accordance with an embodiment. The block diagram 30 includes a server 32, client devices 36.1-36.N, a medical dictionary 38, a protocol names database 40, and a medical report database 42. The server 32 is connected to the client devices 36.1-36.N through network 34. The server 32 is connected to the databases 38, 40 and 42 via network 36. In an embodiment, the network 34 and the network 36 may be the same.

The client devices 36.1-36.N may include an imaging modality, a desktop computer, a mobile computer, and the like. The imaging modality may include a CT modality, an MR modality, and a PET modality. The imaging modalities may include input/output devices that enable a technician for inputting search queries. In an exemplary embodiment, the client devices 36.1-36.N may include a processor and a memory. The memory associated with the client devices 36.1-36.N may include search query generation module 6. The server 32 includes the memory 4, which includes a search query generation module 6, a protocol name identification module 8, and a report generation module 10. The server 32 is configured to accept search queries from the client devices 36.1-36.N. The protocol name identification module 8 is configured for processing the search query for the predefined protocol name. In detail, the search query is processed by extracting keywords from the search query.

The keywords indicate a characteristic of a medical image. The characteristics of a medical image may include, but are not limited to, a body region, examination type, modality type, and protocol description. Based on these terms, the protocol name identification module 8 is configured to determine one or more analogous terms corresponding to the keywords using a medical dictionary database. The medical dictionary database 38 includes analogous or equivalent terms for every term related to the medical or diagnostic field. The medical dictionary database 38 may be indexed based on the terms used in the medicine or diagnostics field. The protocol name identification module 8 retrieves one or more analogous terms for every term in the search query. Thereafter, the protocol name identification module 8 is configured to generate a search phrase based on the one or more analogous terms. The search phrase is used for searching a protocol names database 40 for retrieving relevant predefined protocol names for use in the medical report. In an embodiment, the protocol names database 40 is indexed by associating a medical dictionary term with appropriate predefined protocol names. The server 32 may compute a rank for the protocol names based on best matching criteria. The best matching criteria may include a relevance score associated with the predefined protocol name. Further, the server 32 is configured to select the one or more of the identified predefined protocol names based on the rank associated with the protocol name. The selected predefined protocol name is assigned to a medical report. In an embodiment, the medical report is a Radiation Dosage Structured Report (RDSR). The medical report is rendered searchable using the predefined protocol names. This feature is very helpful during radiation dosage auditing sessions.

Figure 3:
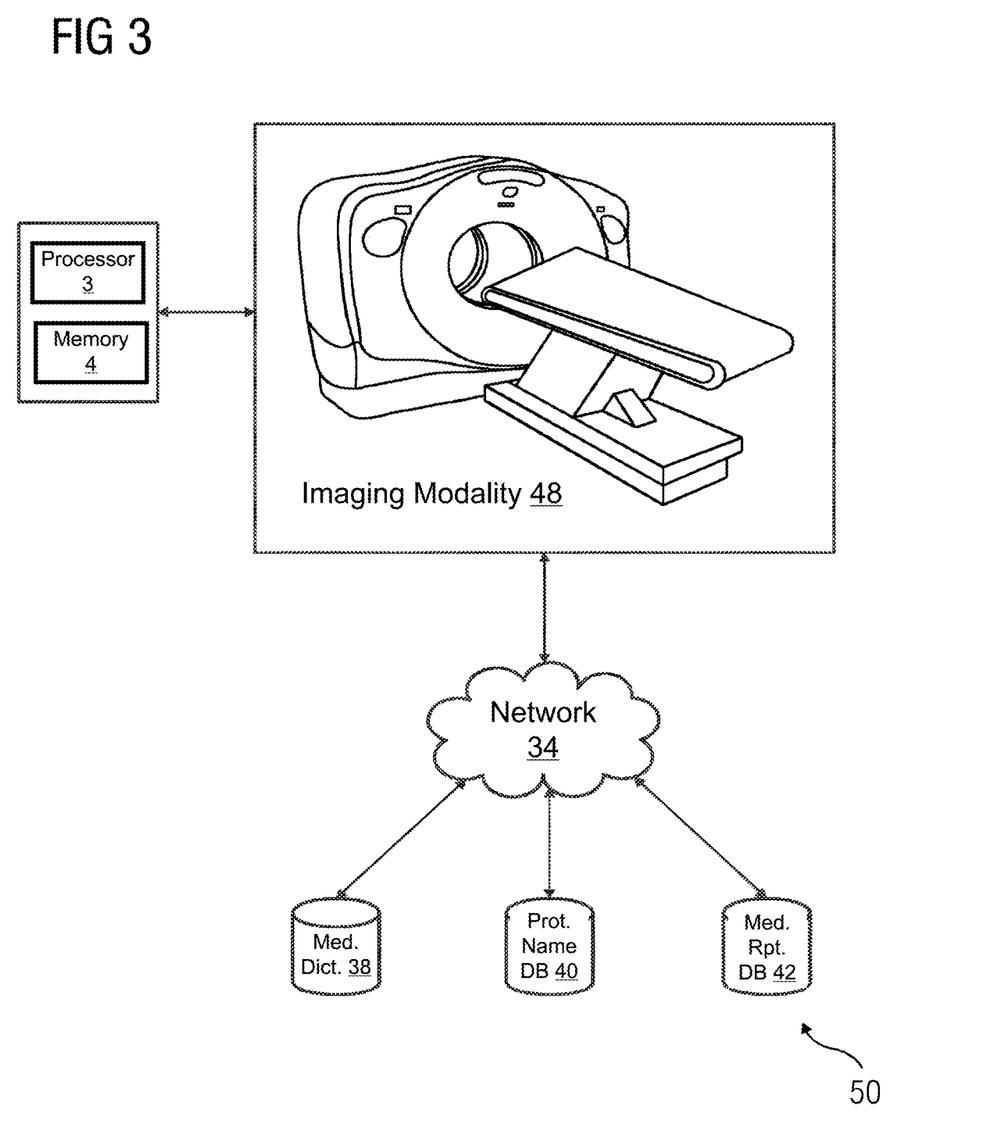
FIG. 3 illustrates an exemplary block diagram of an apparatus for generating medical reports, in accordance with an embodiment.

FIG. 3 illustrates an exemplary diagram of an apparatus 50 for generating medical reports, in accordance with an embodiment in which the server 32 may receive a search query from an imaging modality 48 for searching medical reports based on the predefined protocol names. Once the search query is received, the electronic medical report repository is searched based on the terms in search query. The search query includes a predefined protocol name.

In an embodiment, the apparatus 50 is set up in a cloud computing environment. In such an embodiment, the medical dictionary database 38 and the protocol names database 40 is set up in a cloud environment. The medical dictionary database 38 and the protocol names database 40 are appropriately indexed based on the medical terms. The client devices 36.1-36.N may generate a search query for a predefined protocol name. In an example, the search query is generated by an imaging modality. In another embodiment, the search query may be generated by a technician using the imaging modality. The search query may contain one or more search terms associated with body region, modality type, laterality, population, contrast type, anatomical focus, and reason for exam. For example, body region may include regions of the body such as head and abdomen. Further, laterality may include terms such as bilateral, left, or right. Reason for exam may include, for example, stroke, screw replacement, and trauma. Anatomical focus may include terms such as, but not limited to, pancreas, pulmonary arteries, mandible and coronary arteries.

For example, the technician may type
Body region: Head
Modality Type: CT
Population: Child
Reason for exam: Trauma
The search query is then processed by the server 32. The server 32 extracts analogous or equivalent terms from the medical dictionary database 38, which is deployed in the cloud environment. The server 32 generates a search phrase that includes the search terms along with the analogous terms extracted from the medical dictionary database 38. For example, the search phrase generated by the server 32 may be as below:

Search Phrase: (Head OR Cranium) AND (Computerized Tomography OR CT) AND (Child OR Pediatric) AND (trauma)

The search phrase is used to search the protocol names database 40 for a best matching predefined protocol name to be inserted in the medical report. The protocol names database 40 is indexed based on the terms of the medical dictionary. In an exemplary embodiment, the predefined protocol names in the protocol names database 40 may be indexed using Lucene free-text search engine. Accordingly, the terms of the search phrase are matched with the indexed terms of protocol names database 40, and a set of predefined protocol names are shortlisted. Some exemplary protocol names and the corresponding best matching score are as given in Table 1.

TABLE 1

| Protocol Name | Best Matching score |
|---|---|
| PID_3016 | 6.25 |
| PID_1124 | 5.5 |
| PID_4521 | 4.3 |

The set of the predefined protocol names are presented in the display unit associated with the imaging modality 48. In an embodiment, the shortlisted predefined protocol names may be ranked based on a best matching score. At the imaging modality 48, the technician may select a relevant predefined protocol name to be included in the report using an input device. In an embodiment, a predefined protocol name from the suggested protocol names may be automatically assigned to an appropriate field in the medical report. For example, the technician may select the predefined protocol name PID_3016. Thereafter, the predefined protocol name PID_3016 may be included in the medical report that is generated after performing the imaging procedure on the subject.

Since the databases are deployed in the cloud environment, the recommendation of predefined protocol names may be provided as a service to all the client devices. The protocol name suggestion service may be provided at a hospital level or regional level. The protocol name suggestion service may be used by all the hospitals to have a uniform protocol name in the medical report. For example, the protocol name suggestion service may be used to have a uniform RadLex Playbook ID (RPID) in the RDSR for a particular imaging procedure.

In another embodiment, the medical reports with the predefined protocol names are stored in the medical reports database 42. The medical report database 42 is further indexed based on the predefined protocol names. This enables a user to search the medical records based on predefined protocol names. This feature facilitates the auditing process, as the auditing firm will be able to peruse all the medical records of a particular category. For example, a radiation dosage auditing firm may retrieve all the medical reports having the predefined protocol name PID_3016 in order to examine all the reports with the criteria of Head (body region), CT modality type, population type child, and reason for examination as trauma.

Figure 4:
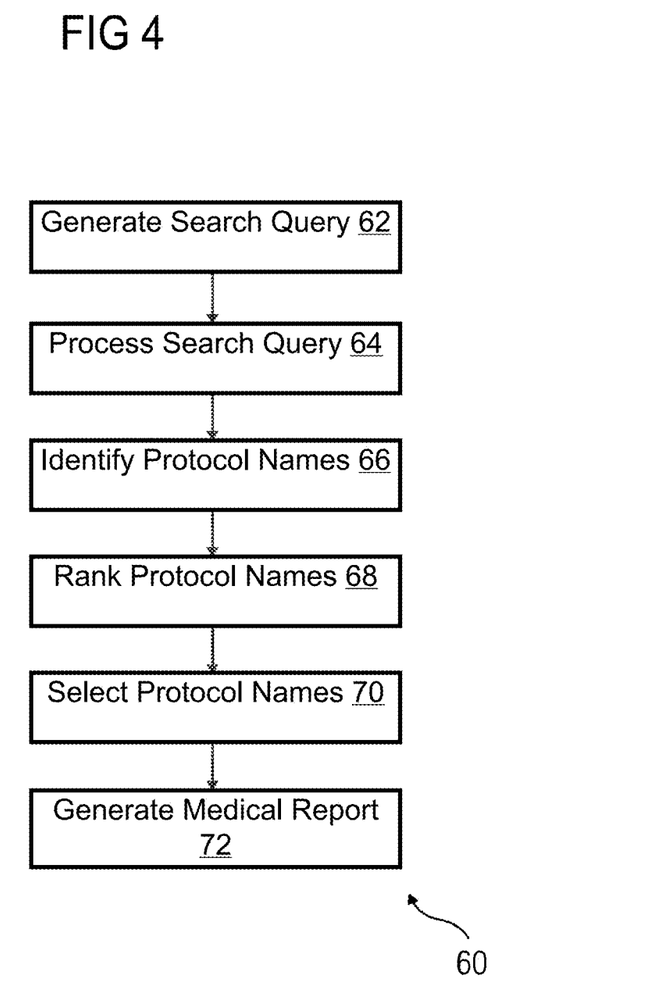
FIG. 4 illustrates a flow diagram of method acts involved in generating a medical report, in accordance with an embodiment.

FIG. 4 illustrates a flow diagram 60 of the method acts involved in generating a medical report, in accordance with an embodiment. At act 62, a search query is generated for a predefined protocol name for the electronic medical report. In an embodiment, the search query is generated by a user before commencing the imaging examination on the patient. In another embodiment, a computing device such as computing device 2 determines at least one characteristic of the medical image and automatically generates a search query based on the at least one characteristic of the medical image. For example, the computing device 2 may determine characteristics of a medical image such as body region, modality type, and exam type from an appointment schedule. Based on this information, the computing device 2 may generate a search query for a predefined protocol name based on the characteristics of the medical image. At act 64, the search query for the predefined protocol names is processed. The search query is processed by extracting keywords that indicate a characteristic of a medical image. Thereafter, one or more analogous terms corresponding to the keywords are determined using a medical dictionary database. A search phrase is generated based on the one or more analogous terms.

At act 66, one or more predefined protocol names are identified from a plurality of protocol names in a protocol names database. The predefined protocol names are identified by comparing the analogous terms in the search phrase with one or more medical dictionary terms in the protocol names database. For the purpose of selecting the predefined protocol names, the protocol names database 40 is indexed based on the medical dictionary terms that are present in the medical dictionary database 38.

Thereafter, one or more predefined protocol names corresponding to the matching terms are retrieved from the protocol names database 40.

At act 68, a rank for the protocol names is computed based on best matching criteria. For example, the best matching criteria may be a relevance of the search phrase with the medical dictionary terms and the number of terms in the search phrase matching with indexed medical dictionary terms.

At act 70, one or more of the identified predefined protocol names are selected based on the rank associated with the protocol name. The predefined protocol names may be selected manually by the technician operating the imaging modality. In another embodiment, the predefined protocol name may be automatically selected based on the rank associated with the predefined protocol name. At act 72, an electronic medical report is generated using the one or more predefined protocol names. Further, the medical reports are rendered searchable using the predefined protocol names. The feature making the medical reports searchable by predefined protocol name is very beneficial during auditing.

The embodiments enable standardization of naming conventions at institutional levels. The need for mapping informal protocol names to standardized names is eliminated, which saves both time and resources. The embodiments enable standardizing the naming convention and mapping the medical records based on the naming convention at a single instance. The protocol name suggestion service based on the embodiments disclosed herein enables the hospitals across the globe to have uniform protocol names for the medical reports such as RDSR. The protocol name suggestion service may be made a part of the workflow of imaging examinations, which speeds up the process of auditing the medical reports such as RDSRs.

While the present invention has been described in detail with reference to certain embodiments, the present invention is not limited to these embodiments. In view of the present disclosure, many modifications and variations would be present to those skilled in the art without departing from the scope of the various embodiments of the present invention, as described herein. The scope of the present invention is therefore indicated by the following claims rather than by the foregoing description. All changes, modifications, and variations coming within the meaning and range of equivalency of the claims are to be considered within their scope.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method of generating an electronic medical report, the method comprising:

generating, using a processor, a search query for a predefined protocol name for the electronic medical report prior to performing a medical imaging procedure associated with the electronic medical report, wherein the predefined protocol name is specific to a body region, a modality type, a laterality, a population, a contrast type, an anatomical a focus, a reason for exam, or a combination thereof, and wherein generating the search query comprises:

determining at least one characteristic of a medical image; and automatically generating the search query based on the at least one characteristic of the medical image;

processing the search query for the predefined protocol name, wherein processing the search query comprises extracting keywords from the search query, the keywords indicating the at least one characteristic of the medical image;

identifying one or more predefined protocol names from a plurality of protocol names in a protocol names database based on the search query;

computing a rank for the one or more predefined protocol names based on a best matching criteria;

displaying the one or more predefined protocol names in order of the rank on a display unit;

selecting the predefined protocol name from the one or more identified predefined protocol names based on the rank associated with the predefined protocol name;

assigning the predefined protocol name to an appropriate field in the electronic medical report prior to performing the medical imaging procedure; and generating the electronic medical report using the one or more predefined protocol names, wherein the electronic medical report is searchable using the predefined protocol name.

2. The method of claim 1, wherein processing the search query further comprises:
- determining one or more analogous terms corresponding to the keywords using a medical dictionary database; and
- generating a search phrase based on the one or more analogous terms.

3. The method of claim 2, wherein identifying the one or more predefined protocol names from the plurality of protocol names comprises:
- comparing the one or more analogous terms in the search phrase with one or more medical dictionary terms in the protocol names database;
- determining the medical dictionary terms matching with the analogous terms in the search phrase; and
- retrieving one or more predefined protocol names corresponding to the matching terms from the protocol names database.

4. The method of claim 1, further comprising:
- indexing the protocol names database, the indexing comprising associating a medical dictionary term with appropriate predefined protocol names.

5. The method of claim 1, further comprising:
- receiving a search request for an electronic medical report, wherein the search request comprises a predefined protocol name;
- searching an electronic medical report repository using the predefined protocol name;
- retrieving the electronic medical report having the predefined protocol name.

6. A computing device for generating an electronic medical report, the computing device comprising:
- a processor;
- a communication module configured to receive a search query for a predefined protocol name for the electronic medical report, the search query being generated prior to performing a medical imaging procedure associated with the electronic medical report and based on at least one characteristic of a medical image, wherein the predefined protocol name is specific to a body region, a modality type, a laterality, a population, a contrast type, an anatomical a focus, a reason for exam, or a combination thereof; and
- a memory coupled with the processor, wherein the memory comprises processor executable instructions, the processor executable instructions comprising:
  - processing the search query for the predefined protocol name;
  - extracting keywords from the search query, wherein the keywords indicate a characteristic of the medical image;
  - identifying one or more predefined protocol names from a plurality of predefined protocol names from a protocol names database based on the search query;
  - assigning a rank for the plurality of predefined protocol names based on a best matching criteria;
  - displaying the plurality of predefined protocol names in order of the rank on a display unit;
  - selecting the predefined protocol name from the plurality of identified predefined protocol names based on the rank associated with the predefined protocol name;
  - assigning the predefined protocol name to an appropriate field in the electronic medical report prior to performing the medical imaging procedure; and
  - generating the electronic medical report based on the one or more predefined protocol names, wherein the electronic medical report is searchable using the predefined protocol name.

7. The computing device of claim 6, wherein processing the search query comprises:
- determining one or more analogous terms corresponding to the keywords using a medical dictionary; and
- generating a search phrase based on the one or more analogous terms.

8. The computing device of claim 6, wherein identifying the one or more predefined protocol names comprises:
- comparing the one or more analogous terms in the search phrase with one or more medical dictionary terms in the protocol names database;
- determining the medical dictionary terms matching with the analogous terms in the search phrase; and
- retrieving one or more predefined protocol names corresponding to the matching terms from the protocol names database.

9. The computing device of claim 6, wherein the processor executable instructions further comprise:
- receiving a search request for an electronic medical report, wherein the search request comprises a predefined protocol name;
- searching an electronic medical report repository using the predefined protocol name of the search request; and
- retrieving the electronic medical report having the predefined protocol name.

10. A system for generating an electronic medical report, the system comprising:
- a server configured to receive search queries from a medical imaging modality;
- a medical imaging modality operatively coupled with the server, wherein the medical imaging modality is configured to acquire a medical image of a subject and to generate an electronic medical report, wherein the medical imaging modality is configured to send search queries to the server, the search queries being generated based on at least one characteristic of a medical image prior to acquiring the medical image; and
- a computing device operatively coupled with the medical imaging modality, wherein the computing device is configured to:
  - extract keywords from a search query, wherein the keywords indicate a characteristic of the medical image;
  - identify one or more predefined protocol names based on the search query wherein each of the one or more predefined protocol names is specific to a body region, a modality type, a laterality, a population, a contrast type, an anatomical a focus, a reason for exam, or a combination thereof;
  - computing a rank for the one or more predefined protocol names based on a best matching criteria;
  - display the one or more predefined protocol names in order of the rank on a display unit;
  - select one predefined protocol name of the one or more identified predefined protocol names based on the rank associated with the one or more predefined protocol name; and
  - assign the one predefined protocol name to an appropriate field in the electronic medical report prior to acquiring the medical image, wherein the electronic medical report is searchable using the predefined protocol name
  - output the one or more identified predefined protocol names on a display unit.

11. The system of claim 10, wherein the server is further configured to:
   index the protocol names database, the index of the protocol names database comprising association of a medical dictionary term with appropriate predefined protocol names.

12. The system of claim 10, wherein the server is further configured to:
   receive a search request for an electronic medical report, wherein the search request comprises a predefined protocol name;
   search an electronic medical report repository using the predefined protocol name;
   retrieve the electronic medical report having the predefined protocol name.

13. The system of claim 10, wherein the server is configured to render the electronic medical report searchable by at least one field that comprises the predefined protocol name.

* * * * *